United States Patent
Zarembo et al.

(10) Patent No.: US 7,486,994 B2
(45) Date of Patent: Feb. 3, 2009

(54) METHOD AND DEVICE FOR SUPPORTING OR STRENGTHENING A PORTION OF A LEAD

(75) Inventors: Paul E. Zarembo, Vadnais Heights, MN (US); Gregory R. Ley, Blaine, MN (US); Brian D. Soltis, St. Paul, MN (US); Daniel L. Cox, Palo Alto, CA (US); Brett Cryer, Sunnyvale, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 545 days.

(21) Appl. No.: 10/243,625

(22) Filed: Sep. 13, 2002

(65) Prior Publication Data

US 2004/0054390 A1 Mar. 18, 2004

(51) Int. Cl.
*A61N 1/06* (2006.01)

(52) U.S. Cl. ..................................................... 607/116

(58) Field of Classification Search .................. 607/5, 607/37, 116, 119, 122, 36; 439/445–448
See application file for complete search history.

(56) References Cited

U.S. PATENT DOCUMENTS

| | | | | |
|---|---|---|---|---|
| 2,101,713 A | * | 12/1937 | Jolliffe | 439/448 |
| 2,616,684 A | * | 11/1952 | Richter | 267/166.1 |
| 3,800,068 A | * | 3/1974 | Torgerson | 174/135 |
| 4,314,095 A | * | 2/1982 | Moore et al. | 174/84 C |
| 4,632,488 A | * | 12/1986 | Long et al. | 439/452 |
| 5,007,435 A | * | 4/1991 | Doan et al. | 607/119 |
| 5,170,802 A | | 12/1992 | Mehra | 128/784 |
| 5,423,865 A | | 6/1995 | Bowald et al. | 607/5 |
| 5,431,683 A | | 7/1995 | Bowald et al. | 607/5 |
| 5,439,485 A | | 8/1995 | Mar et al. | 607/119 |
| 5,517,989 A | * | 5/1996 | Frisbie et al. | 600/585 |
| 5,531,779 A | | 7/1996 | Dahl et al. | 607/119 |
| 5,713,945 A | | 2/1998 | Fischer et al. | |
| 5,728,149 A | * | 3/1998 | Laske et al. | 607/122 |
| 5,775,331 A | | 7/1998 | Raymond et al. | 128/741 |
| 5,823,817 A | * | 10/1998 | Pyle | 439/447 |
| 5,824,031 A | | 10/1998 | Cookston et al. | 607/122 |
| 5,851,226 A | | 12/1998 | Skubitz et al. | 607/126 |
| 5,897,584 A | | 4/1999 | Herman | 607/122 |
| 5,954,761 A | | 9/1999 | Macheck et al. | 607/126 |
| 6,078,839 A | | 6/2000 | Carson | 607/116 |
| 6,094,596 A | | 7/2000 | Morgan | 607/5 |
| 6,161,029 A | | 12/2000 | Spreigl et al. | 600/381 |
| 6,192,277 B1 | | 2/2001 | Lim et al. | 607/37 |

(Continued)

OTHER PUBLICATIONS

Definition of "coil spring" from dictionary.com.*

*Primary Examiner*—Carl H Layno
*Assistant Examiner*—Frances P Oropeza
(74) *Attorney, Agent, or Firm*—Schwegman, Lundberg & Woessner, P.A.

(57) ABSTRACT

A lead assembly and method of forming a lead assembly is provided. Devices and methods of forming the lead assembly include a support coil. The support coil provides enhanced support and protection from lead damage and failure. A lead assembly and method of forming a lead assembly is also provided including at least one electrode. Electrodes may be incorporated into the support coil design. The lead assembly and method of forming a lead assembly may be incorporated with other medical devices such as an implantable defibrillator.

23 Claims, 6 Drawing Sheets

U.S. PATENT DOCUMENTS

| | | | |
|---|---|---|---|
| 6,219,577 B1 | 4/2001 | Brown, III et al. | 604/20 |
| 6,264,598 B1 * | 7/2001 | Armini | 600/3 |
| 6,445,954 B1 | 9/2002 | Olive et al. | 607/37 |
| 2003/0083724 A1 * | 5/2003 | Jog et al. | 607/122 |

* cited by examiner

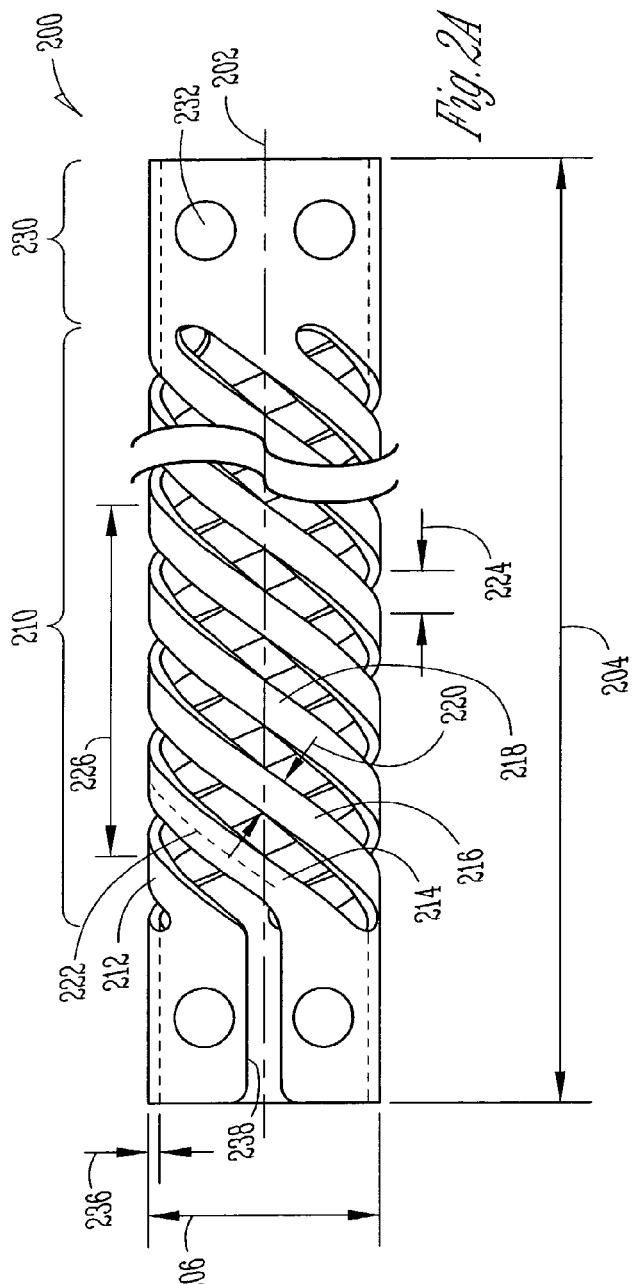
Fig. 2A
Fig. 2B
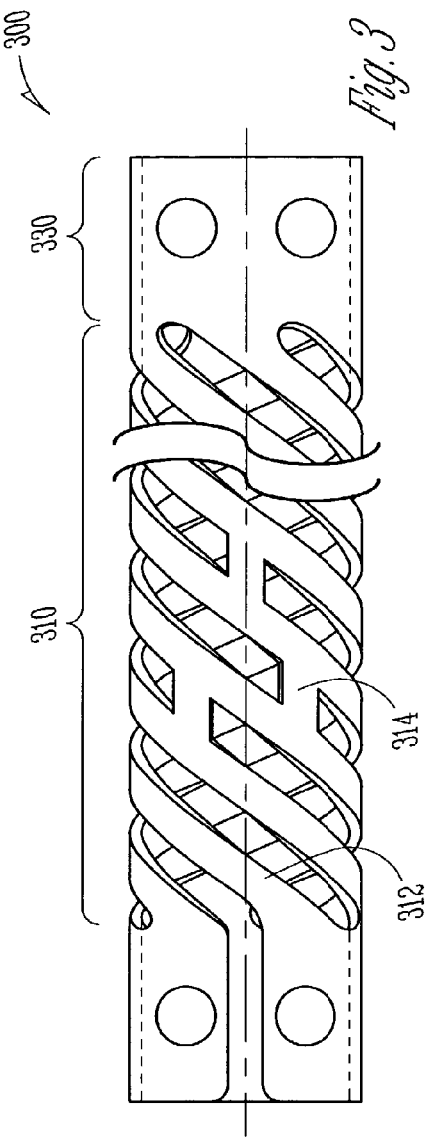
Fig. 3

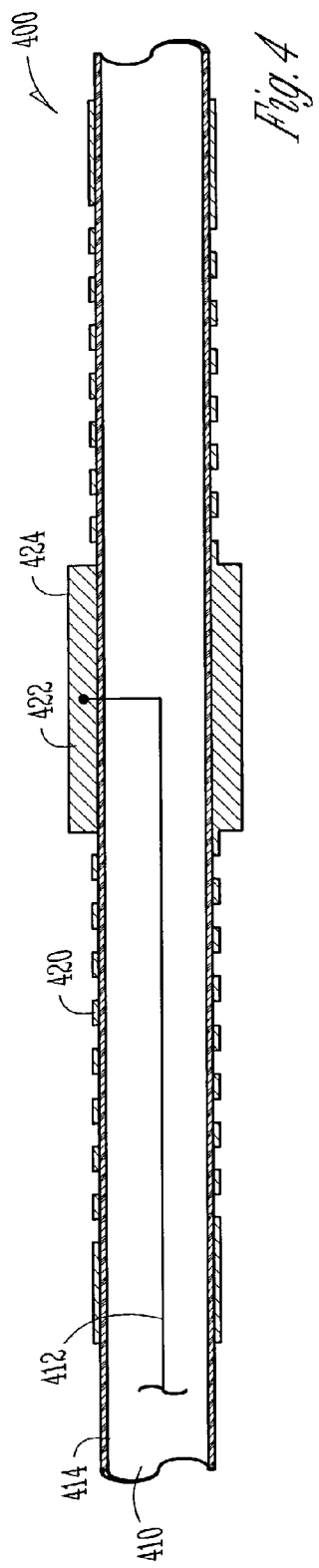
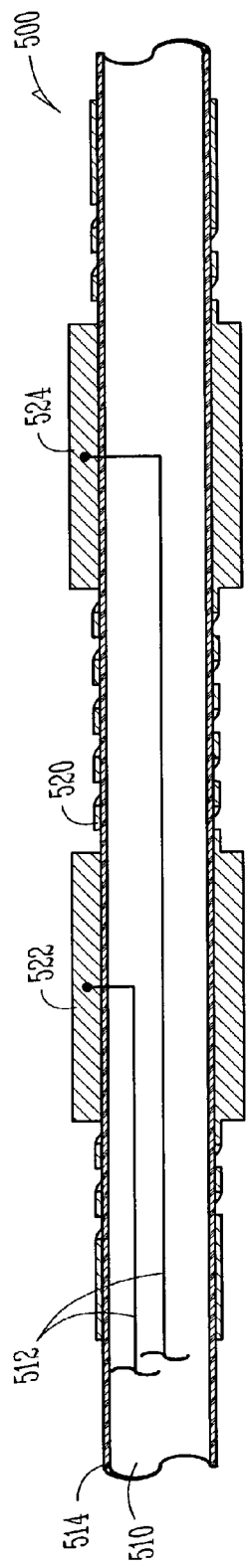
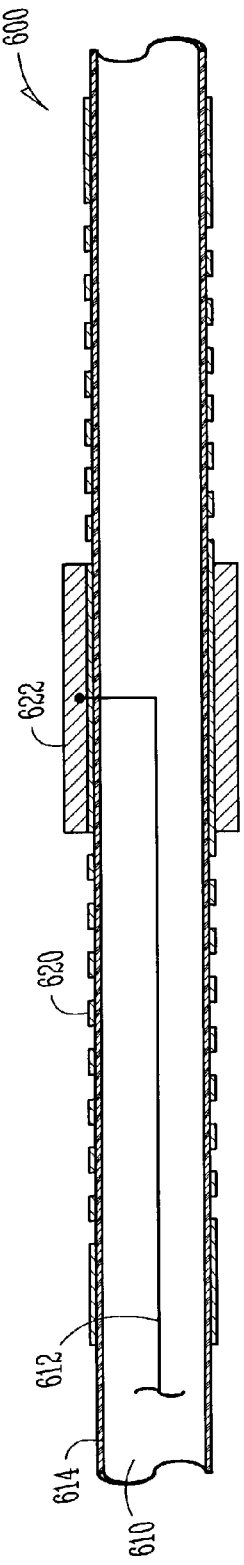

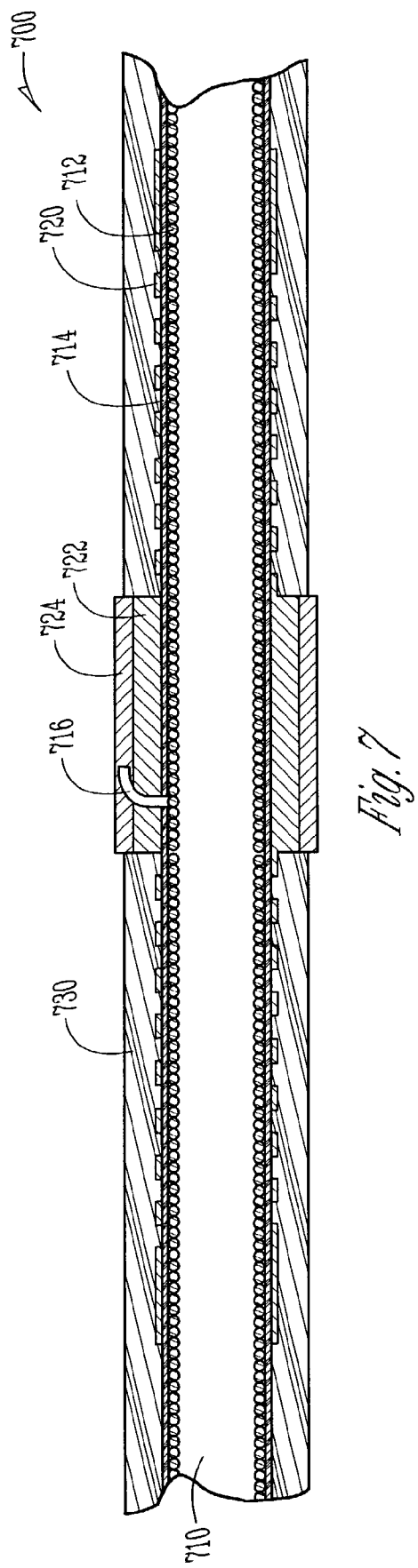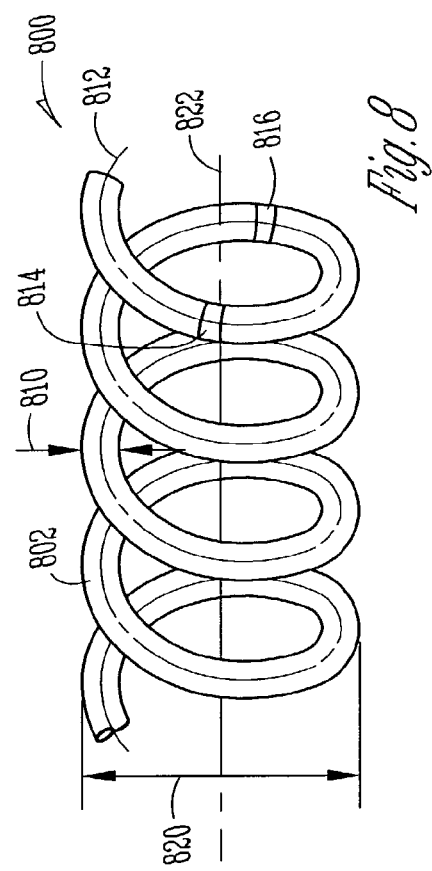

METHOD AND DEVICE FOR SUPPORTING OR STRENGTHENING A PORTION OF A LEAD

FIELD OF THE INVENTION

The present invention concerns implantable medical devices, such as defibrillators and cardioverters, and more specifically a lead for an implantable medical device.

BACKGROUND

Implantable defibrillators detect the onset of abnormal heart rhythms and apply corrective electrical therapy, specifically one or more bursts of electric current to the heart. A defibrillator assembly includes a set of electrical leads, which extend from a pulse generator housing into the heart. Within the pulse generator housing are a battery for supplying power, monitoring circuitry for detecting abnormal heart rhythms, and a capacitor for delivering the bursts of electric current through the leads to the heart. Since the pulse generator portion of the defibrillator assembly is usually implanted in the left region of the chest or in the abdomen, the leads must extend from that area through veins and into the heart.

During normal daily activity of a patient, the leads must flex through a large number of cycles and withstand various other stresses. Numerous cycles of flexing causes fatigue damage and failure in leads, and other stresses such as axial stress can further cause lead damage. Leads are particularly susceptible to fatigue damage or failure at stress concentration points along the lead. Examples of stress concentration points include, but are not limited to where a lead exits a pulse generator, or where a lead is attached to a more rigid structure such as an electrode. Kinking in a flexural direction and crushing in an axial direction may also be problems in stress concentration points.

Leads may need to follow narrow and tortuous paths which may require short electrodes to navigate tight bends, thus creating more stress concentration points. Additionally, the designed size of leads is decreasing with industry pressure to make less invasive products. Smaller leads tend to be more fragile, which further increases the need for more robust lead designs that can withstand numerous flex cycles and axial stresses.

What is needed is a lead that is more robust and resistant to damage or failure from modes such as fatigue failure, axial damage or failure, or other lead stress failure modes. What is also needed is an electrode and lead design that is flexible and adds axial strength while maintaining a small lead diameter.

SUMMARY

The above mentioned problems with lead damage and failure are addressed by the present invention and will be understood by reading and studying the following specification. Devices and methods are provided for a more robust lead design.

A lead assembly is shown that includes a lead. The lead includes an electrical conductor and a flexible insulator coupled to the electrical conductor, the flexible insulator electrically isolating a portion of the electrical conductor. The lead assembly also includes a support structure having an inner surface. The inner surface is coupled to the lead at a selected axial location along the lead and providing structural support to the lead.

Other embodiments may include at least one electrical tissue contact surface coupled to the support structure and coupled to the electrical conductor. In other embodiments, a medical device such as an implantable defibrillator is coupled to the lead assembly.

In one embodiment, the lead assembly includes a stent-like support structure having an inner surface. The inner surface is coupled to the lead at a selected axial location along the lead and providing structural support to the lead.

A method of manufacturing a lead assembly is also shown, the method includes forming a lead. Forming the lead includes forming an electrical conductor and coupling a flexible insulator to a portion of the electrical conductor. The method of manufacturing a lead assembly also includes forming a support coil. Forming the support coil includes forming at least one filar; shaping a number of filar turns; and coupling an inner surface of the support coil to the lead at a selected axial location along the lead.

Other embodiments may include coupling at least one electrical tissue contact surface to the support coil and coupling the electrical tissue contact surface to the electrical conductor. In other embodiments, the method includes coupling a medical device such as an implantable defibrillator to the lead assembly.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

BRIEF DESCRIPTION OF THE DRAWINGS

FIG. 2A shows a side view of one embodiment of a support coil.

FIG. 2B shows an end view of one embodiment of a support coil.

FIG. 3 shows a side view of another embodiment of a support coil.

FIG. 4 shows a portion of one embodiment of a lead assembly.

FIG. 5 shows a portion of another embodiment of a lead assembly.

FIG. 6 shows a portion of another embodiment of a lead assembly.

FIG. 7 shows a portion of another embodiment of a lead assembly.

FIG. 8 shows a portion of another embodiment of a lead assembly.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

In this document, references to coordinates with respect to leads or lead assemblies will refer to axial locations and radial locations. Longitudinal or axial locations are locations along a longitudinal axis of a lead or lead assembly. Radial locations will use the conventional 2-dimensional radial coordinates (r, θ) in a circle that is normal to the longitudinal axis. The term lateral side will refer to surfaces or portions of a surface that is substantially parallel to a longitudinal axis. It should be noted that leads are generally flexible, and do not always lie along a straight line, however, a linear model will be used for ease of discussion.

Figure 1A:
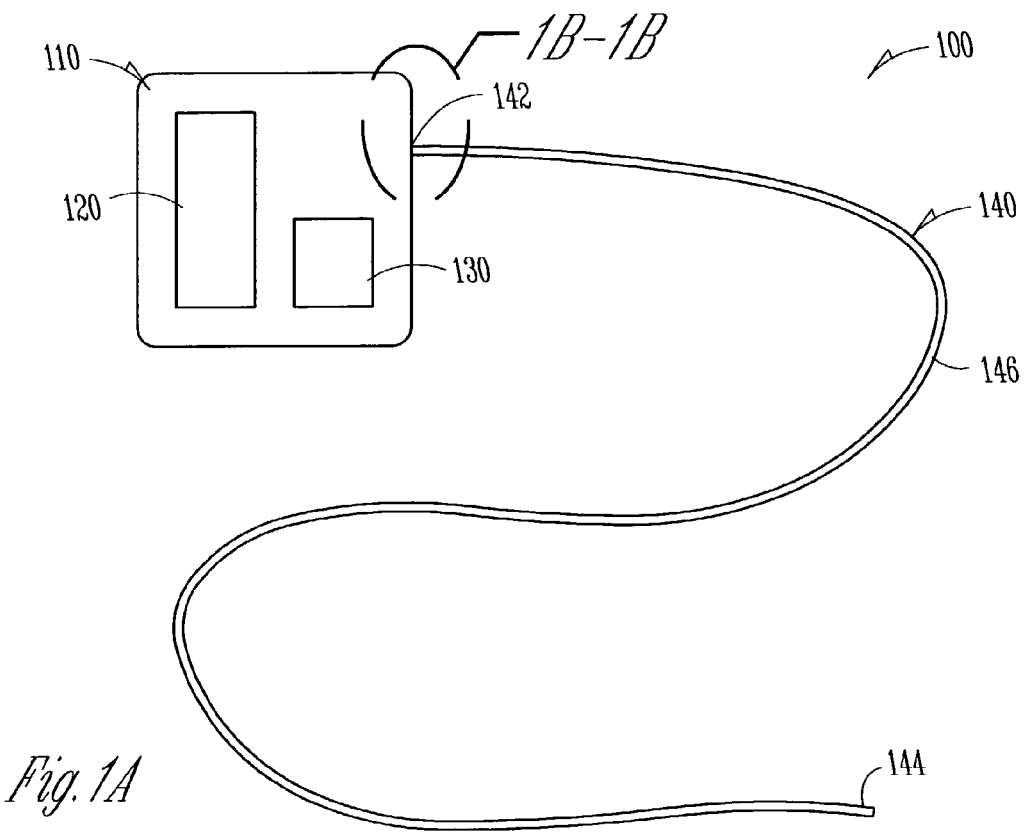
FIG. 1A shows one embodiment of an implantable defibrillator assembly.

FIG. 1 shows an implantable defibrillator assembly 100 according to one embodiment of the invention. The implantable defibrillator assembly 100 includes a pulse generator 110 and a lead assembly 140. Although an implantable defibrillator 100 is used to illustrate embodiments of the invention, the invention is not limited to implantable defibrillators. Other medical devices using a lead assembly 140 are also within the scope of the invention. The pulse generator 110 includes a power source 120 such as a battery, and monitoring circuitry 130. The lead assembly 140 includes a lead 146, with a proximal end 142 and a distal end 144.

Figure 1B:
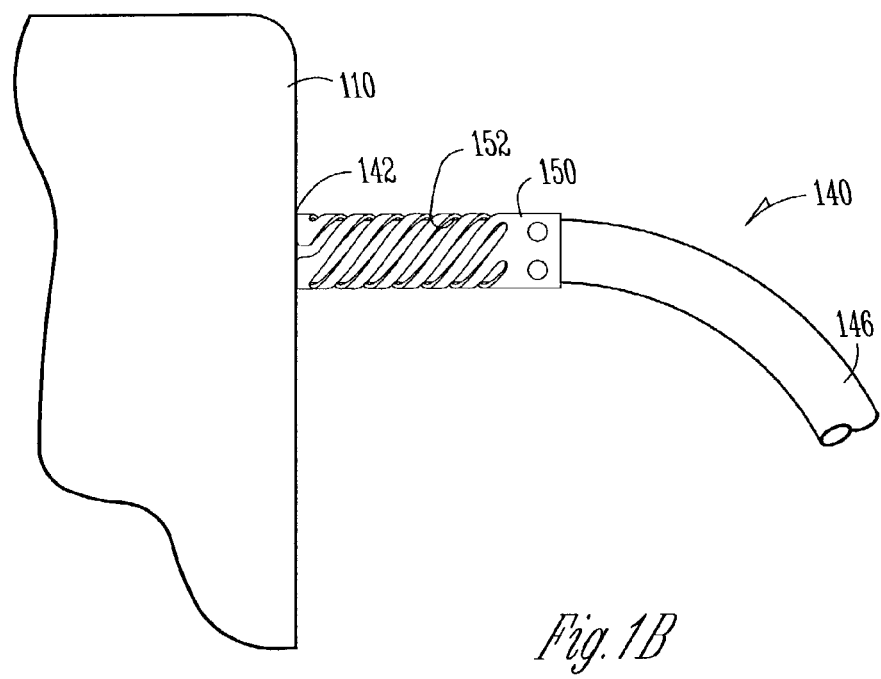
FIG. 1B shows a magnified view of a portion of one embodiment of an implantable defibrillator assembly.

FIG. 1B shows the proximal end 142 of the lead 146 in magnified detail where the lead assembly 140 interfaces with the pulse generator 110. The lead assembly 140 includes a support coil 150, shown attached at the proximal end 142 of the lead 146, and attached to the pulse generator 110. In one embodiment, an interface 152 is formed between an inner surface of the support coil 150 and an outer surface of the proximal end 142 of the lead assembly 140. In one embodiment, the interface 152 is continuous across the entire inner surface of the support coil 150. Other embodiments include a non-continuous interface 152, however, sufficient interfacial contact between the support coil 150 and the lead 146 is utilized to provide structural support for the lead 146.

Structural support includes, but is not limited to lateral flexural support, and axial support. Lateral flexural support includes support to resist stresses and fatigue resulting from any radial deflection of a portion of the lead 146 from a longitudinal axis of the lead 146. Axial support includes support to resist stresses such as tensile stress, compressive stress, and sheer stress that may occur as a result of a force being applied to a lead in a direction substantially parallel to the longitudinal axis.

FIG. 2A shows one embodiment of a support coil 200. The support coil 200 includes a radial thickness 236, with an outer coil diameter 206. An inner coil surface 234 is also indicated in FIG. 2B. The support coil 200 includes a coil portion 210 and, in one embodiment, the support coil 200 includes a collar portion 230. In one embodiment, the coil portion 210 and the collar portion 230 are centered around a coil axis 202. In one embodiment, the support coil includes a stent-like support structure. A stent-like support structure includes several possible designs of stent "walls" that are designed to provide axial and flexural support. A stent-like support structure in embodiments of the present invention, however, is not required to expand or contract radially as is functionally required by actual stents.

The embodiment shown in FIG. 2A includes a pair of collar portions 230. One or more collar portions 230 are included in selected embodiments for structure and for bonding integrity with the lead. Multiple collar portions 230 are included on alternate embodiments for additional support or bonding strength. The support coil 200 in one embodiment is attached to a lead using an interference fit. A collar portion 230 adds structural support in interference fit embodiments by providing additional spring force in the radial direction of the lead assembly. In other embodiments, the support coil is attached to a lead using an adhesive. In an adhesive embodiment, the collar portion 230 provides additional surface area for bonding strength.

In one embodiment, the collar portion includes a bonding feature 232. Through-thickness openings or etched features, etc. are included as possible bonding features 232. A circular through hole is shown in FIG. 2A as an example of a bonding feature 232. Other bonding feature shapes include, but are not limited to, oblong holes, slots, angled cut outs, etc. Although two bonding features 232 are shown in the collar portion 230 in FIG. 2A, single bonding features or other numbers of bonding features are also acceptable. The collar portion 230, in one embodiment, includes a slot 238. In one embodiment, the slot 238 also serves as a bonding feature.

The bonding features 232 increase the bonding strength in both an adhesive mechanism and a mechanical mechanism. The bonding features 232 increase a bond interface area, thus increasing adhesive bond strength. Additionally, the bonding features 232 provide mechanical strength. A cured adhesive that has flowed into and around a bonding feature 232 such as a through-thickness opening, must shear or deform in order to fail rather than merely separate at a bond interface.

The coil portion 210 includes one or more filars. In one embodiment, the filars include flat portions with a substantially rectangular cross section. Various other cross sections, such as square, elliptical, and circular cross sections are included in alternate embodiments. Embodiments with a single filar, or various numbers of filars are within the scope of the application. For example, the embodiment shown in FIG. 2A includes four filars, a first filar 212, a second filar 214, a third filar 216, and a fourth filar 218. Each filar includes a radial cross section width 220. The width 220 within each filar, in one option, can be varied along a filar axis 222. The variations in width affect the physical properties of the support coil 200. Another variable in support coil design includes a filar pitch 224. The pitch can also be varied to affect the physical properties of the support coil 200. Another variable in support coil design includes a filar turn 226. A filar turn 226 is defined as a section of a filar that travels around a circumference of the support coil once. A number of filar turns over a given axial length of the coil portion 210 can also be varied to affect the physical properties of the support coil 200.

The support coil as described above, provides some flexibility, while also providing a level of structural support such as flexural support and axial support. By tailoring various features of the support coil 200, as described above, a physical property of the support coil 200, such as stiffness, is adjusted to the structural needs of a location along a lead.

Further, by tailoring the features of the support coil as described above, a gradient of axial stiffness and flexural stiffness in selected embodiments is tailored at individual locations along an axial length of the support coil.

In one embodiment, the support coil 200 is etched from a single piece of metal starting material. In other embodiments, the support coil is laser cut. In one embodiment, the support coil is electropolished after laser cutting. In one embodiment, a flat starting material is first etched or laser cut and subsequently formed into a substantially tubular member. In one embodiment, a substantially flat starting material is welded into a substantially tubular member.

Possible starting material metals include, but are not limited to NITINOL, stainless steel, MP35N, tantalum, titanium, alloy combinations of the above, etc. Materials other than metal, such as polymers, may also be used as starting materials. In one embodiment, surfaces that will be exposed inside the patient further include a coating of a bio-compatible material. Examples of bio-compatible materials include, but are not limited to, iridium oxide (IROX), platinum, titanium, tantalum, silver, etc. Bio-compatible materials are attached by methods that may include, but are not limited to, ion bombardment, sputtering, electroplating, electroless plating, etc.

FIG. 3 shows another embodiment of a support coil. A support coil 300 is shown, including a coil portion 310 and a collar portion 330. The support coil 300 includes a number of filars 312 that form the coil portion 310. Also included in the support coil 300 are a number of linking features 314 that join filar turns together. In the embodiment shown in FIG. 3, four filars are included in the coil portion 310, with linking features 314 between different filars. The linking features 314 may also be used to link between turns of a single filar embodiment. The linking features 314 may be formed using various methods. Methods include, but are not limited to integrally etching the linking features 314 with the filars 312, or joining separately formed linking features 314 to filars 312 by adhesive, mechanical, thermal, etc. techniques.

The linking features 314 in one embodiment, serve as additional bonding features as described above. In one embodiment, the linking features modify support coil properties such as lateral coil stiffness and axial coil stiffness of the support coil 300.

Embodiments of the support coil described above are attached to a lead at any of a number of axial locations along a lead of a lead to provide added structural support. Using the example illustrated in FIG. 1B, the support coil 150 is flexible, and provides resilient support for the lead 146 at stress concentration points such as the proximal end 142. The support coil increases resistance to fatigue damage or failure, and increases resistance to axial damage or failure by providing added structural support to the lead.

In a further embodiment, the support coil is integrated with other lead components such as an electrode. The area of a lead around a rigid component such as an electrode is subjected to increased fatigue, axial stresses, and/or bonding stress in the rigid component area. These rigid component areas therefore benefit from embodiments of the present invention.

FIG. 4 shows a lead assembly 400 including a lead 410. The lead 410, in one embodiment, includes a conductor 412 (shown in schematic form) and an insulator 414 for selectively isolating the conductor 412. A support coil 420 is shown coupled to the lead 410. In one embodiment, the support coil 420 is structurally and electrically attached to the conductor 412 of the lead 410. In another embodiment, the support coil 420 is structurally attached to the insulator 414, with an electrode 422 separately coupled to, or in electrical communication with the conductor 412.

The electrode 422 of the support coil 420 includes a tissue contact surface 424. In one embodiment, the electrode 422 is centered axially on the support coil 420. Other axial locations along the support coil are also included within the scope of the application. The electrode 422 in one embodiment is integrally formed with the support coil 420. In one embodiment, the support coil 420 including the electrode 422 are etched from a single piece of metal starting material. Possible metals include, but are not limited to NITINOL, stainless steel, MP35N, tantalum, titanium, alloy combinations of the above, etc. Materials other than metal, such as polymers, may also be used as starting materials. In one embodiment, the tissue contact surface 424 further includes a bio-compatible material. Examples of bio-compatible materials include, but are not limited to, iridium oxide (IROX), platinum, titanium, tantalum, silver, etc. The bio-compatible material is attached by a method that may include, but is not limited to, ion bombardment, sputtering, electroplating, electroless plating, etc.

In one embodiment, the support coil 420 is bonded to the lead 410. Bonding features similar to those described above may be used to attach the support coil 420 to the lead 410 in bonded embodiments. Methods other than bonding are also contemplated for attachment of the support coil 420 to the lead 410, such as mechanical attachment.

FIG. 5 shows a lead assembly 500 including a lead 510. The lead includes a conductor group 512 (shown in schematic form), and an insulator 514 for selectively isolating the conductor group 512. The conductor group 512 may include a single conductor, or a number of conductors. A support coil 520 is shown coupled to the lead 510. In the embodiment shown in FIG. 5, a first electrode 522 and a second electrode 524 are coupled to the support coil 520, which is in turn coupled to the lead 510. Although a single support coil is shown in FIG. 5 with a number of electrodes coupled to the support coil 520, a number of support coils may also be used to accommodate the number of electrodes. In one embodiment, the first electrode 522 and the second electrode 524 are coupled to separate, individual conductors within the conductor group 512 of the lead 510.

FIG. 6 shows a lead assembly 600 including a lead 610. The lead may include a conductor 612 (shown in schematic form) and an insulator 614 for selectively isolating the conductor 612. A support coil 620 is shown coupled to the lead 610. An electrode 622 is further coupled to the support coil 620. In the embodiment shown in FIG. 6, the electrode is a separate component that is attached to the support coil. In one separate component embodiment, the electrode is formed from a bio-compatible material, while the support coil is formed from a different material. In some embodiments, attachment of a separate bio-compatible electrode is less expensive to manufacture than coating an electrode. Methods of attachment include, but are not limited to, welding, spot welding, laser welding, thermal fitting, memory metal fitting, staking, swaging, crimping, threading, bonding, etc.

FIG. 7 shows another embodiment of a lead assembly 700 including a lead 710, a support coil 720, a tissue contact surface 724, and an outer isolation layer 730. The lead includes an electrical conductor 712 and an insulator layer 714. In one embodiment, the electrical conductor is formed in a coil shape within the insulator layer 714.

The support coil 720 is coupled to the lead 710 by structural attachment to the insulator layer 714. Examples of structural attachment include, but are not limited to adhesive attachment and mechanical attachment. An electrode region 722 is included on the support coil 720 in a central location of the support coil 720. The tissue contact surface 724 is further coupled to the electrode region 722 of the support coil 720. In one embodiment, the electrode region 722 is integrally formed with the support coil 720, and the tissue contact surface 724 is separately attached. One skilled in the art, with the benefit of the present specification, will understand that other variations of integral forming and separate attachment are possible within the scope of the application.

An electrical contact 716 is included in one embodiment to communicate electrically between the electrical conductor 712 and the tissue contact surface 724. The isolation layer 730 is included in selected embodiments to further isolate the support coil 720 from an environment such as inside the human body. In one embodiment, the isolation layer 730 includes a polymer layer.

FIG. 8 shows an embodiment of a lead assembly 800. A lead 802 is included with a conductor diameter 810, and a conductor axis 812. The lead 802 is formed into a spiral shape with a spiral diameter 820 and a spiral axis 822. Further included on the lead assembly 800 are a first electrode 814, and a second electrode 816. Although two electrodes are shown, a single electrode, or a number of electrodes may also be used. In one embodiment, the electrodes 814 and 816 are coupled to an embodiment of a support coil as described above.

In operation, a form such as the spiral shown in FIG. 8 is formed on a distal end of a lead assembly, and used to hold the distal end of the lead assembly in place within a blood vessel, or other location within a patient. Formed leads may also be used to aid in guiding or tracking of the lead during a procedure such as insertion. One skilled in the art, having the benefit of the present disclosure will recognize that electrodes need not be included on embodiments where improved tracking of a lead is desired. In one embodiment, a support structure as described in the present disclosure is utilized to support a formed portion of a lead such as a spiral shape, or other shapes. Although a spiral shape is shown, other embodiments are contemplated where a portion of the lead 802, such as a distal end, is formed into a bend, or shape that deviates from an axis of the rest of the lead 802. It should be noted that conductor assemblies are designed to be flexible. A shape formed into a portion of the lead 802, such as a distal end should be characterized relative to a normal, unstressed state of the lead 802.

FIGS. 9-14 show support structures that are alternatives to embodiments of support coils as described above. The term support structure is defined to include support coils, but not be limited to coil structures such as filars.

Figure 9:
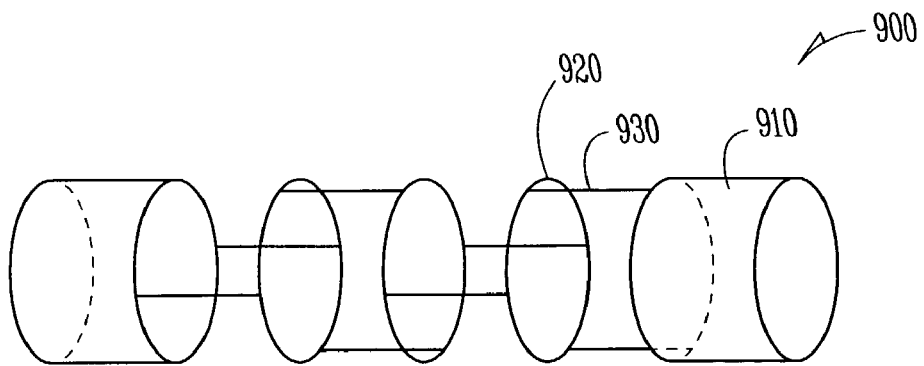
FIG. 9 shows a side view of one embodiment of a support structure.

FIG. 9 shows a support structure 900. In one embodiment, the support structure 900 includes at least one collar portion 910. The support structure 900 includes at least one ring member 920 and a number of connecting members 930. The connecting members 930 all provide axial support for a lead assembly. The connecting members 930 also provide flexural support to a lead assembly depending on their location around a circumference of the support structure 900. In one embodiment, the connecting members 930 primarily provide flexural support due to flexing of the connecting members 930. Flexing of the connecting members 930 typically provides a larger possible range of motion in the lead, in contrast to tensile deformation of the connecting members 930. In one embodiment, therefore, connecting members are spaced about the circumference of the support structure 900 to provide connecting members to flex in a number of different possible lead bending directions.

Figure 10:
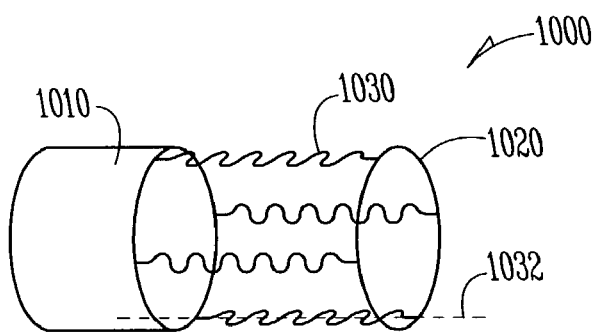
FIG. 10 shows a side view of one embodiment of a support structure.

FIG. 10 shows a support structure 1000. In one embodiment, the support structure 1000 includes at least one collar portion 1010. The support structure 1000 includes at least one ring member 1020 and a number of connecting members 1030. In one embodiment, the connecting members 1030 include serpentine structures. The serpentine structures 1030 all provide axial support for a lead assembly. The serpentine structures 1030 also provide flexural support to a lead assembly. In one embodiment, the serpentine structures 1030 provide flexural support in both a flexing mode, and a tensile mode. In the tensile mode, the serpentine structures 1030 extend and contract along their individual long axes 1032.

Figure 11:
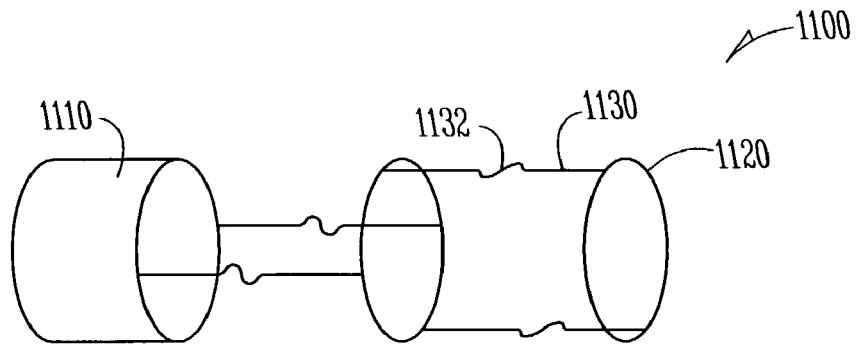
FIG. 11 shows a side view of one embodiment of a support structure.

FIG. 11 shows a support structure 1100. In one embodiment, the support structure 1100 includes at least one collar portion 1110. The support structure 1100 includes at least one ring member 1120 and a number of connecting members 1130. In one embodiment, the connecting members 1130 include individual serpentine bends 1132. The connecting members 1130, as well as the serpentine bends 1132 all provide axial support for a lead assembly. The serpentine bends 1132 also provide flexural support to a lead assembly. In one embodiment, the serpentine bends 1132 provide flexural support in both a flexing mode, and a tensile mode. In the tensile mode, the serpentine bends 1132 extend and contract along individual long axes. A number of serpentine bends 1132 can be varied within each connecting member 1130 to further tailor support properties of the support structure 1100.

Figure 12:
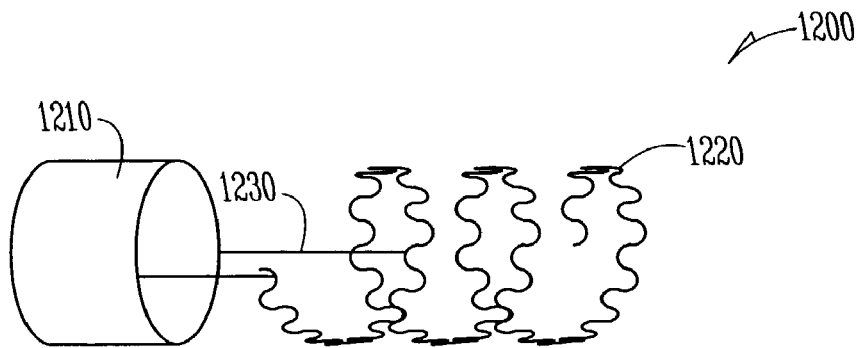
FIG. 12 shows a side view of one embodiment of a support structure.

FIG. 12 shows a support structure 1200. In one embodiment, the support structure 1200 includes at least one collar portion 1210. The support structure 1200 includes a spiral structure 1220 and a number of connecting members 1230. In one embodiment the spiral structure 1220 includes a serpentine structure. The spiral structure 1220 provides axial support as well as flexural support to a lead assembly. In one embodiment, the serpentine structure provide flexural support in both a flexing mode, and a tensile mode. In the tensile mode, the serpentine structure of the spiral structure 1220 extends and contract along a axial length of the serpentine structure.

Figure 13:
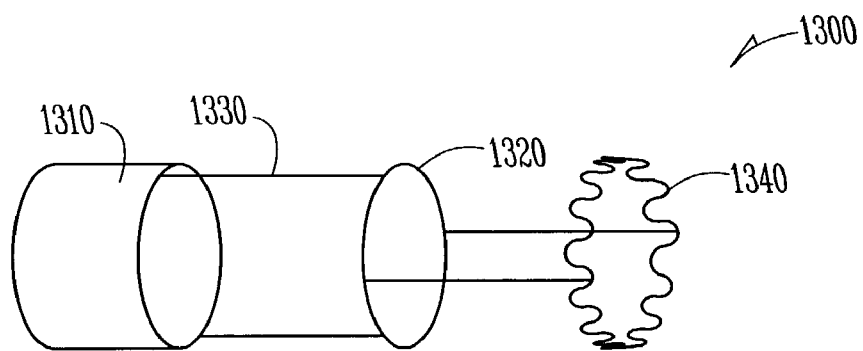
FIG. 13 shows a side view of one embodiment of a support structure.

FIG. 13 shows a support structure 1300. In one embodiment, the support structure 1300 includes at least one collar portion 1310. The support structure 1300 includes a ring structure 1320 and a number of connecting members 1330. The support structure 1300 further includes a holding device 1340. In one embodiment, the holding device 1340 includes a serpentine structure attached at to itself at its ends to form a ring. The holding device 1340 provides some degree of axial and flexural support to a lead assembly. In one embodiment, the holding device 1340 primarily provides a mechanical bond for an end of the support structure 1300, similar to bonding of a collar portion as described in embodiments above. A serpentine structure, as shown in FIG. 13, provides a "hoop force" along the circumference of the ring shaped holding device 1340. The hoop force grips a lead assembly and holds an end of the support structure 1300 in place. Although one holding device 1340 is shown in FIG. 13, two holding devices 1340 at opposing ends of the support structure 1300 are included in other embodiments. Additional holding devices 1340 may also be included along the longitudinal axis of the support structure 1300.

Figure 14:
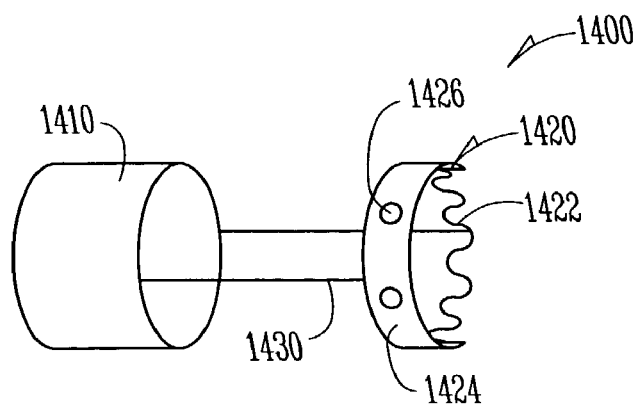
FIG. 14 shows a side view of one embodiment of a support structure.

FIG. 14 shows a support structure 1400. In one embodiment, the support structure 1400 includes at least one collar portion 1410. The support structure 1400 includes a hybrid holding device 1420 and a number of connecting members 1430. In one embodiment, the hybrid holding device 1420 includes a portion of serpentine structure 1422 and a portion of collar structure 1424. In one embodiment, the portion of serpentine structure 1422 is attached to the portion of collar structure 1424 to form a ring shaped hybrid holding device 1420. The portion of collar structure 1424 provides structural rigidity and a good bonding surface, while the portion of serpentine structure 1422 provides a degree of flexibility in the hybrid holding device 1420. In one embodiment, the portion of collar structure 1424 further includes at least one bonding feature 1424 similar to embodiments described above. Although one hybrid holding device 1420 is shown in FIG. 14, two hybrid holding devices 1420 at opposing ends of the support structure 1400 are included in other embodiments. Additional hybrid holding device 1420 may also be included along the longitudinal axis of the support structure 1400.

Thus a lead assembly and method of manufacturing a lead assembly is shown that is more robust and resistant to damage or failure from modes such as fatigue failure, axial damage or failure, or other lead stress failure modes. A support structure as described above is used to enhance the lead at selected axial locations of the lead, such as stress concentration locations. As shown above, stress concentration locations include locations where the lead is attached to a more rigid body such as a pulse generator housing or an electrode.

The embodiments of support structures and support coils as described above maintain a degree of flexibility, while spreading out lateral flexing stresses at stress concentration points over a larger axial region. The spreading of the lateral flexing stresses reduces fatigue failure. The stiffness of the lead assembly can be tailored over the axial length of the support structure as described above to further enhance the spreading of lateral flexing stresses.

Additionally, axial stresses are reduced by employing various embodiments of support structures as described above. Local axial stresses at stress concentration points are also spread out over a larger axial region due to an increased interfacial area and stronger bond between the support structure and the lead. The additional axial support reduces axial failures including, but not limited to, bond failures around electrodes.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A lead assembly, comprising:
   a tissue stimulator lead, including:
      an electrical conductor;
      a flexible insulator coupled to the electrical conductor, the flexible insulator electrically isolating a portion of the electrical conductor; and
      a support structure having an inner surface, an outer surface, and one or more bordering collar portions, the inner surface surrounding an outer surface of the lead at a selected axial location along the lead and providing lengthwise varying structural support to the lead, the one or more collar portions including at least one bonding feature void extending from the support structure outer surface to the support structure inner surface positioned adjacent the lead outer surface,
   wherein the support structure is electrically isolated from the electrical conductor via the flexible insulator.

2. The lead assembly of claim 1, wherein the support structure includes a support coil, the support coil being comprised of at least one filar having a number of filar turns.

3. The lead assembly of claim 1, wherein substantially all portions of a circumference of the lead are engaged by at least a portion of the support structure.

4. The lead assembly of claim 2, wherein the support coil includes multiple filars.

5. The lead assembly of claim 2, wherein a filar cross sectional dimension is varied along a filar length.

6. The lead assembly of claim 2, wherein a filar pitch is varied along a length of the support coil.

7. The lead assembly of claim 1, wherein a longitudinal axis of the support structure falls along a single straight line in an unstressed state.

8. The lead assembly of claim 1, wherein a portion of a longitudinal axis of the support structure is formed into a spiral.

9. The lead assembly of claim 2, wherein the support coil further includes a plurality of non-contiguous, non-linear linking features between filar turns.

10. The lead assembly of claim 1, wherein the support structure material includes a polymer.

11. The lead assembly of claim 1, wherein the lead includes a preformed bias portion at the selected axial location, and wherein at least a portion of the support structure surrounds and supports the outer surface of the lead at the bias.

12. An implantable assembly, comprising:
    a pulse generator, including:
       an electrical supply source;
       a control circuit;
    a lead assembly coupled to the pulse generator, including:
       an at least partially implantable lead, including:
          an electrical conductor;
          a flexible insulator coupled to the electrical conductor, the flexible insulator electrically isolating a portion of the electrical conductor; and
          a support coil having an inner surface and one or more bordering collar portions, the inner surface surrounding an outer surface of the lead at a selected axial location along the lead adjacent one or more tissue electrodes and providing structural support to the lead, the one or more bordering collar portions including at least one bonding feature void in communication with the lead outer surface;
    wherein a flexural stiffness along a length of the support coil varies to spread lateral flexing stress away from one or more lead stress concentration locations.

13. The implantable assembly of claim 12, wherein a second support coil is located at a stress concentration location between the lead assembly and the pulse generator.

14. The implantable assembly of claim 12, wherein the support structure includes a support coil, the support coil being comprised of at least one filar having a number of filar turns.

15. The implantable assembly of claim 12, wherein substantially all portions of a circumference of the lead are engaged by at least a portion of the support structure.

16. The implantable assembly of claim 14, wherein the support coil includes multiple filars.

17. The implantable assembly of claim 14, wherein a filar cross sectional dimension is varied along a filar length.

18. The implantable assembly of claim 14, wherein a filar pitch is varied along a length of the support coil.

19. The implantable assembly of claim 14, wherein the support coil further includes a number of spaced apart, non-linear linking features between filar turns.

20. The implantable assembly of claim 12, wherein the support structure is formed from a metal.

21. The implantable assembly of claim 12, wherein the support coil is integrated with at least one tissue electrode.

22. The implantable assembly of claim 21, wherein an electrical tissue contact surface of the at least one tissue electrode includes one or a combination of iridium oxide, platinum, titanium, tantalum, or silver.

23. The implantable assembly of claim 21, wherein the at least one tissue electrode includes at least a first and a second tissue electrode.

* * * * *